(12) United States Patent
Suh et al.

(10) Patent No.: US 7,939,669 B2
(45) Date of Patent: *May 10, 2011

(54) METALLIC COMPOUND AND ORGANIC ELECTROLUMINESCENCE DEVICE COMPRISING THE SAME

(75) Inventors: Dong-Hack Suh, Seongnam (KR); Jin-Sik Choi, Seoul (KR); Jin-Soo Lim, Seoul (KR); Song-Ho Kim, Seoul (KR); Chi-Hun Kim, Seoul (KR)

(73) Assignees: Samsung Electronics Co., Ltd. (KR); Industry-University Cooperation Foundation, Hanyang University (KR)

( * ) Notice: Subject to any disclaimer, the term of this patent is extended or adjusted under 35 U.S.C. 154(b) by 129 days.

This patent is subject to a terminal disclaimer.

(21) Appl. No.: 11/913,192

(22) PCT Filed: Jan. 8, 2007

(86) PCT No.: PCT/KR2007/000111
§ 371 (c)(1),
(2), (4) Date: Oct. 31, 2007

(87) PCT Pub. No.: WO2007/078182
PCT Pub. Date: Jul. 12, 2007

(65) Prior Publication Data
US 2009/0306395 A1    Dec. 10, 2009

(30) Foreign Application Priority Data
Jan. 6, 2006    (KR) .................. 10-2006-0001727

(51) Int. Cl.
C07D 277/62    (2006.01)
C07D 263/54    (2006.01)
(52) U.S. Cl. ......... 548/152; 548/146; 548/215; 548/217

(58) Field of Classification Search .................. 548/146, 548/152, 159, 215, 217, 219
See application file for complete search history.

(56) References Cited

U.S. PATENT DOCUMENTS
6,703,146 B1    3/2004    Sakaguchi et al.

FOREIGN PATENT DOCUMENTS
| | | |
|---|---|---|
| JP | 2003007471 | 1/2003 |
| JP | 2003077675 | 3/2003 |
| JP | 2003171659 | 6/2003 |
| JP | 2003264086 | 9/2003 |

OTHER PUBLICATIONS

International Search Report; PCT/KR2007/000111; Apr. 11, 2007.
Highly Phosphorescent Bis-Cyclometalated Iridium Complexes; Synthesis, Photophysical Characterization, and Use in Organic Light Emitting Diodes, J. Am. Chem. Soc. 2001, 123,4304-4312.
Synthesis and Characterization of Phosphorescent Cyclometalated Iridium Complexes; Sergey Lamansky, Peter Djurovich, Drew Murphy, Feras Abdel-Razzaq, Raymond Kwong, Irina Tsyba, Manfred Bortz, Becky Mui, Robert Bau, and Mark E. Thompson; Imorg. Chem. 2001, 40, 1704-1711.
New, efficient electroluminescent materials based on organometallic Ir complexes; Vladimir V. Grushin,, Norman Herron, Daniel D. LeCloux, William J. Marshall, Viacheslav A. Petrov and Ying Wang; Chem. Commun. 2001, 1494-1495.
Written Opinion; PCT/KR2004/000111; Apr. 11, 2007.

*Primary Examiner* — Golam M Shameem
(74) *Attorney, Agent, or Firm* — Cantor Colburn LLP

(57) ABSTRACT

The present invention relates to a light emitting transition metal compound of Chemical Formula 1 and an organic electroluminescence device including the compound.
In the Chemical Formula 1, M is selected from Ir, Pt, Rh, Re, and Os, m is 2 or 3, n is 0 or 1, the sum of m and n is 3, provided that the sum of m and n is 2 M is Pt. X is a N or P atom, and Y is S, O, or Se.

1 Claim, No Drawings

METALLIC COMPOUND AND ORGANIC ELECTROLUMINESCENCE DEVICE COMPRISING THE SAME

TECHNICAL FIELD

The present invention relates to a metallic compound and an organic electroluminescence device including the same, and more particularly, to a metallic compound that is applicable as a highly efficient phosphor host material and an organic electroluminescence device including the same.

BACKGROUND OF ART

An electroluminescence device (EL device) is a self-light emitting display device having such merits as a wide viewing angle and excellent contrast as well as a quick response time.

EL devices are classified into an inorganic EL device and an organic EL device in accordance with a material used for a light emitting layer. The organic EL device has merits of improved luminance, driving voltage, response speed, and multi-colorfying property compared to an inorganic EL device.

An organic EL device is generally composed of an anode on a substrate, a hole transport layer on the anode, and a light emitting layer, an electron transport layer (ETL), and a cathode sequentially positioned thereon. The hole transport layer, light emitting layer, and electron transport layer (ETL) are organic films that are composed of organic compounds.

The organic EL device having the above structure is operated as follows.

When a voltage is applied to a space between the anode and the cathode, the holes are injected from the anode to the light emitting layer through the hole transport layer. Meanwhile, when the electrons are injected from the cathode into the light emitting layer through the electron transport layer (ETL), carriers are recombined in the region of the light emitting layer to thereby produce excitons. The state of the excitons is changed from an exited state to a base state, and the change in the state of the excitons makes the molecules of the light emitting layer emit light to thereby form an image.

Materials for forming a light emitting layer are divided into fluorescent materials using singlet excitons and phosphorescent materials using triplet excitons according to the light emitting mechanism. Phosphorescent materials generally include organic/inorganic compound structures including transition metal atoms. The transition metal atoms change triplet excitons, which used to be impossible to transition, into excitons that are possible to transition, causing them to emit phosphorescent light. Since the phosphorescent materials can use triplet excitons having a generation probability of 75%, higher luminous efficiency can be achieved than with fluorescent materials using singlet excitons having a generation probability of 25%.

Among light emitting materials using the triplet excitons are phosphorescent materials including iridium and platinum compounds (Sergey Lamansky et al. Inorg. Chem., 40, 1704-1711, 2001, and Sergey Lamansky et al., J. Am. Chem. Soc., 123, 4304-4312, 2001). For blue light emitting materials, Ir compounds based on $(4,6-F2\ ppy)_2Irpic$ or a fluorinated ppy ligand structure have been developed (Vladimir V. Grushin et al., Chem. Commun., 1494-1495, 2001). The $(4,6-F2\ ppy)_2Irpic$, however, has shortcomings that it emits light in a sky blue region and its large shoulder peaks increase a y value in color purity coordinates. Researchers are studying red and green light emitting materials, but there still remains great demand to develop highly efficient phosphorescent materials having a long lifespan.

DETAILED DESCRIPTION OF THE INVENTION

Technical Problem

In order to solve the problems, the object of the present invention is to provide a phosphor metallic compound having a new ligand structure and an organic electroluminescence device having improved luminous efficiency and color purity.

Technical Solution

The present invention relates to a light emitting transition metal compound represented by the following Chemical Formula 1 and an organic electroluminescence device including the same:

Technical Solution

The present invention relates to a light emitting transition metal compound represented by the following Chemical Formula 1 and an organic electroluminescence device including the same.

[Chemical Formula 1]

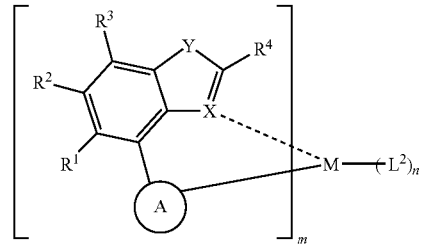

Wherein, M is a transition metal selected from Ir, Pt, Rh, Re, Os, and the like, m is 2 or 3, n is 0 or 1, the sum of m and n is 3, provided that the sum of m and n is 2 when M is Pt, X is N or P, Y is S, O, or Se,

of the Chemical Formula 1 is represented by the following Chemical Formulae 2:

[Chemical Formulae 2]

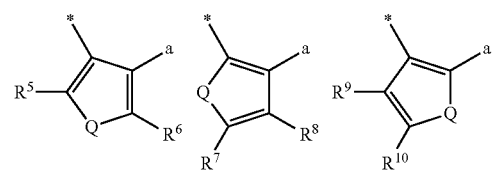

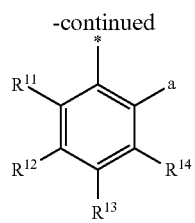

Wherein, in the above Chemical Formulae 2, * denotes a portion that is covalently bound with adjacent aromatic portion, the transition metal M forms a complex while bound with a portion denoted as "a" in the above Chemical Formulae 2 by a covalent bond and bound with X of the Chemical Formula 1 by a coordination bond, $R^1$-$R^3$, and $R^5$-$R^{14}$ are hydrogen, a $C_1$ to $C_{20}$ alkyl, an aryl, a cycloalkyl, a halogen, a linear or branched substituent including at least one halogen, a linear or branched substituent including at least one heteroatom, carbonyl, vinyl, or acetylenyl, or form a cycle, and the same or different, and $R^4$ is hydrogen, a $C_1$ to $C_{20}$ alkyl excluding an aromatic cyclic substituent, a cycloalkyl, a halogen, a linear or branched substituent including at least one halogen; or a linear or branched substituent including at least one heteroatom. In the above Chemical Formula 1, $L^2$ is represented by the following Chemical Formulae 3, 4, and 5:

[Chemical Formulae 3]

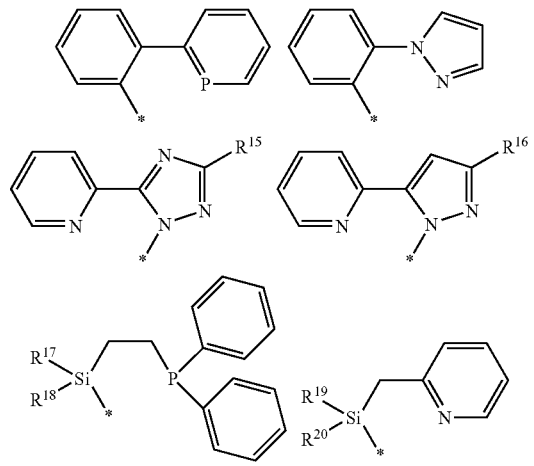

[Chemical Formula 4]

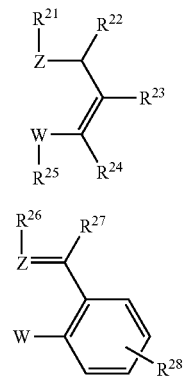

[Chemical Formula 5]

Wherein, the transition metal, M forms a complex by a covalent bond with a portion denoted as * in the above Chemical Formulae 3, and a coordination bond with an adjacent N or P atom, Z and W in the above Chemical Formulae 4 and 5 are the same or different, and a heteroatom of O, N, S, or P, and $R^{15}$-$R^{28}$ in the Chemical Formulae 3, 4, and 5 are the same or different, and selected from hydrogen, a $C_1$ to $C_{20}$ alkyl, an aryl, a cycloalkyl, a halogen, a linear or branched substituent including at least one halogen, a linear or branched substituent including at least one heteroatom, carbonyl, vinyl, or acetylenyl, or may form a cycle. In order to reduce concentration quenching, a functional group having a large steric hindrance such as an alkyl, an aryl, halogen, silyl, and so on is independently included in benzooxazole or benzothiazole, and an aryl. Several nm of light-emission and light wavelength can be easily controlled in accordance with the positions of substituents and properties of electron donors or acceptors. The ligands of the present invention are represented by the following chemical Chemical Formulae 6.

[Chemical Formulae 6]

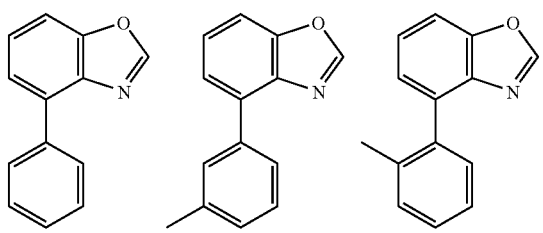

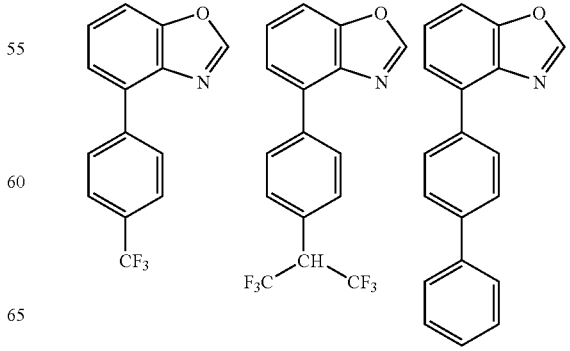

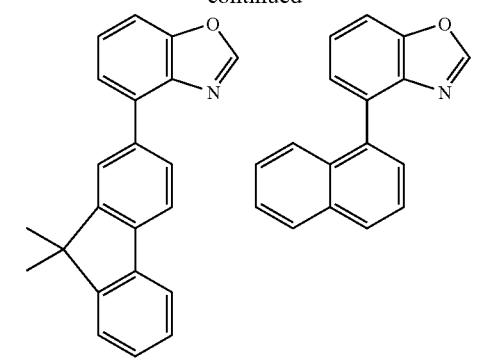
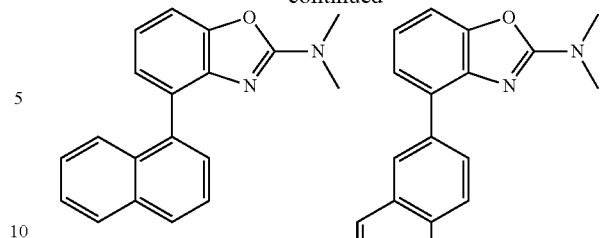
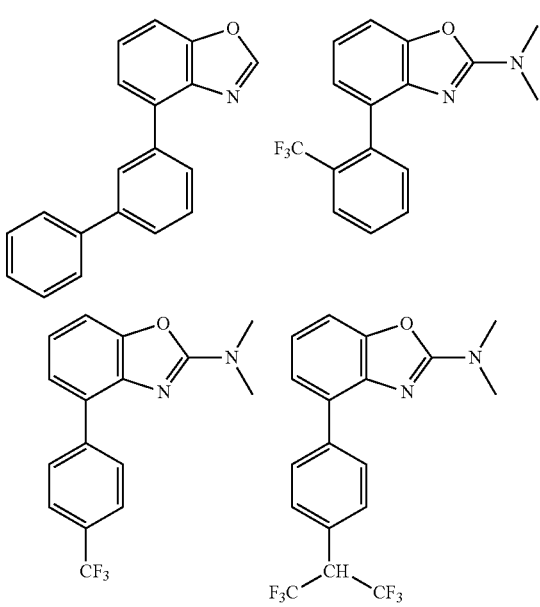
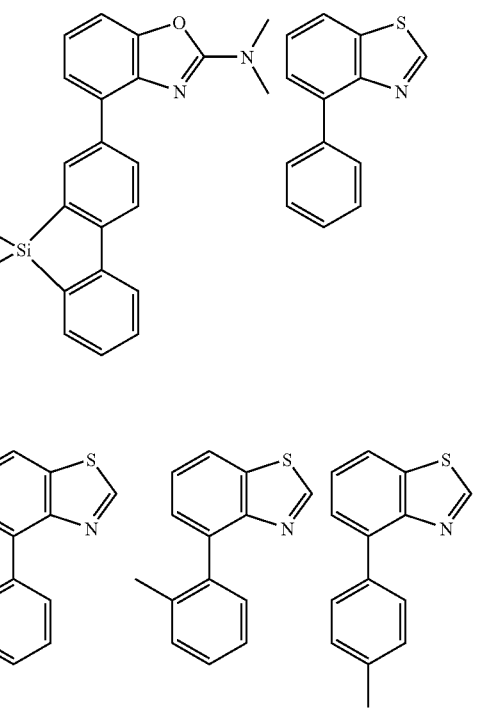
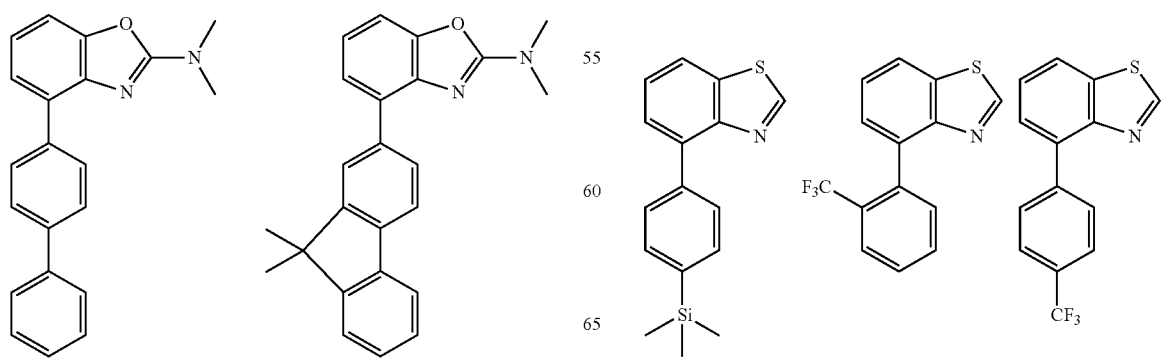

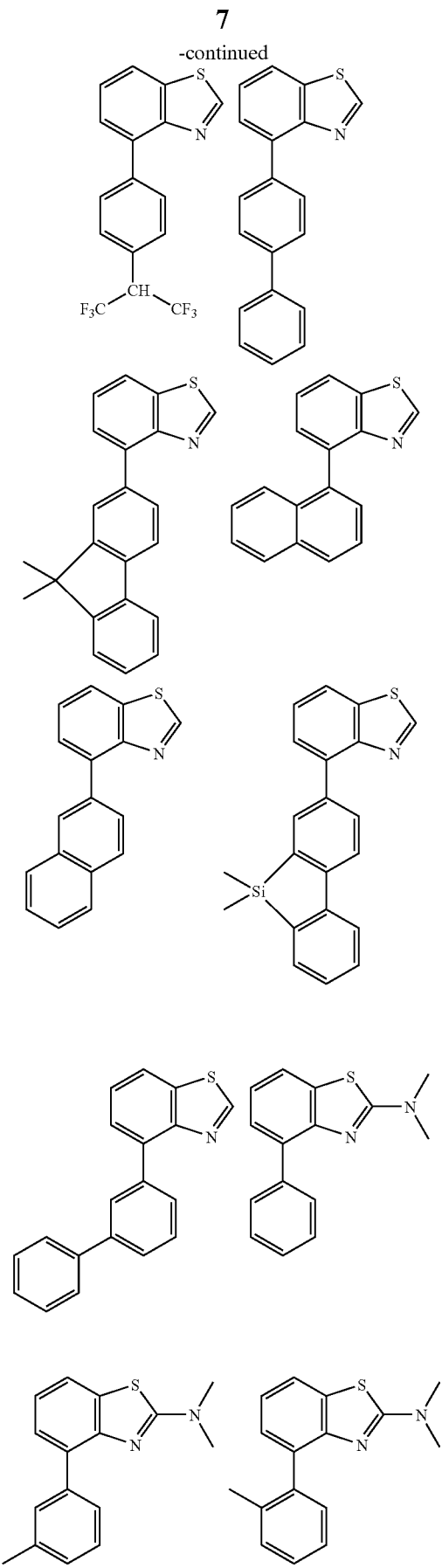
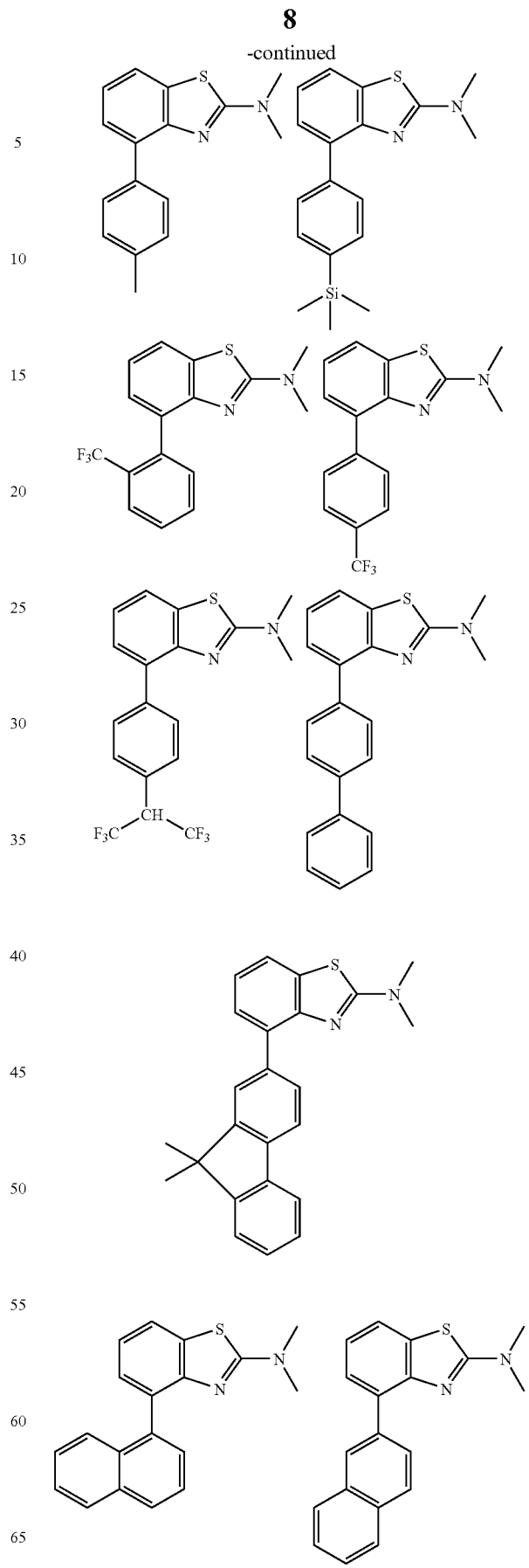

-continued
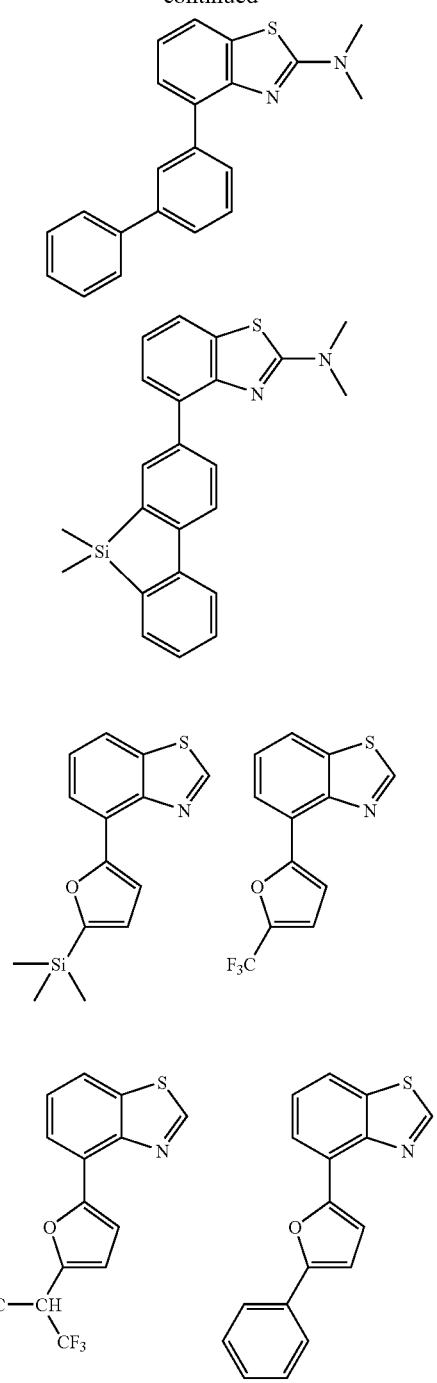
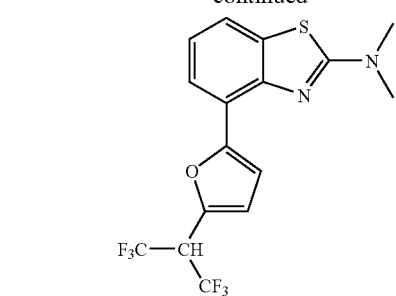
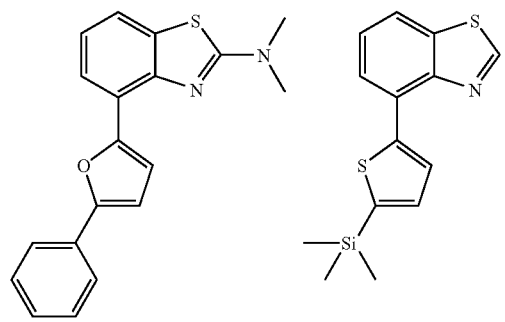
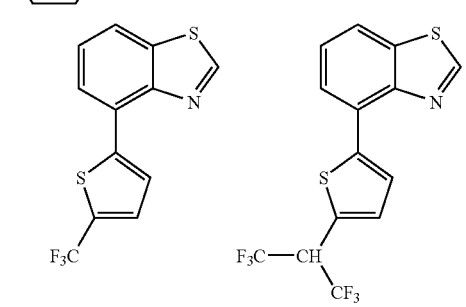
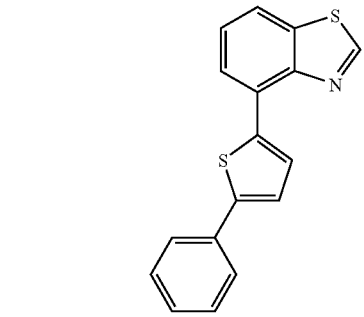
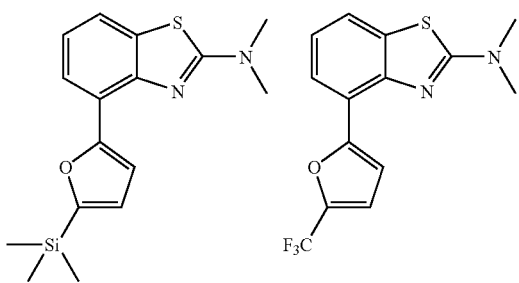
An auxiliary ligand can change a small range of wavelength, and examples of the Auxiliary ligand are represented by the following Chemical Formulae 7:
[Chemical Formulae 7]
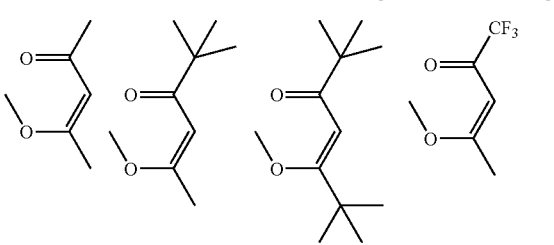

-continued
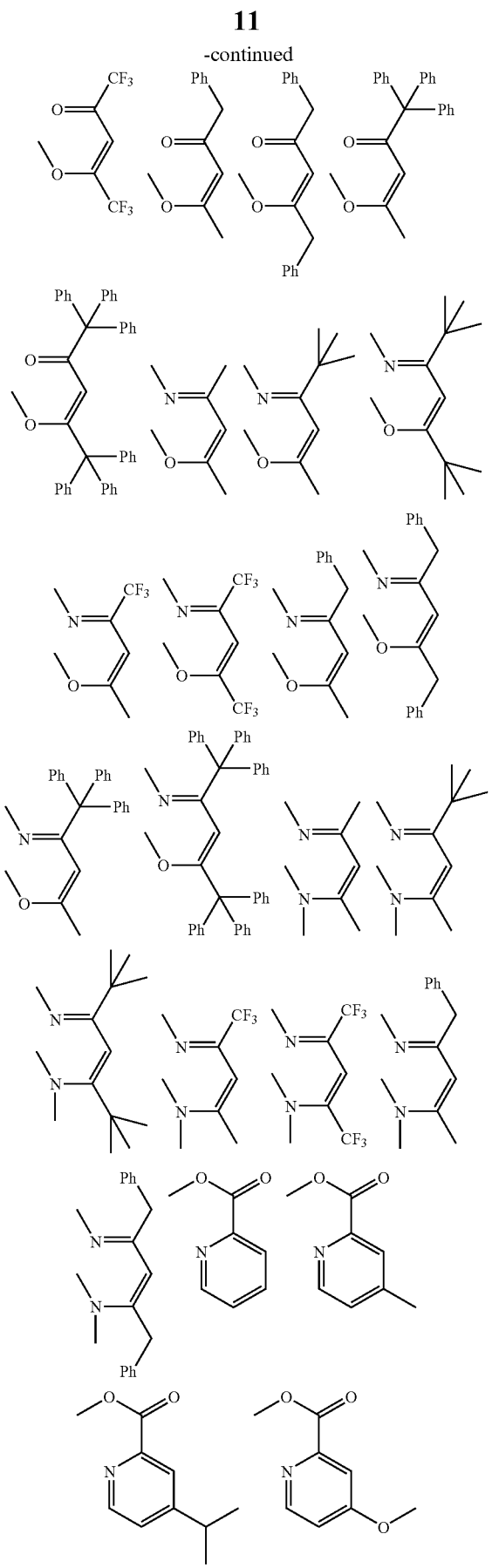
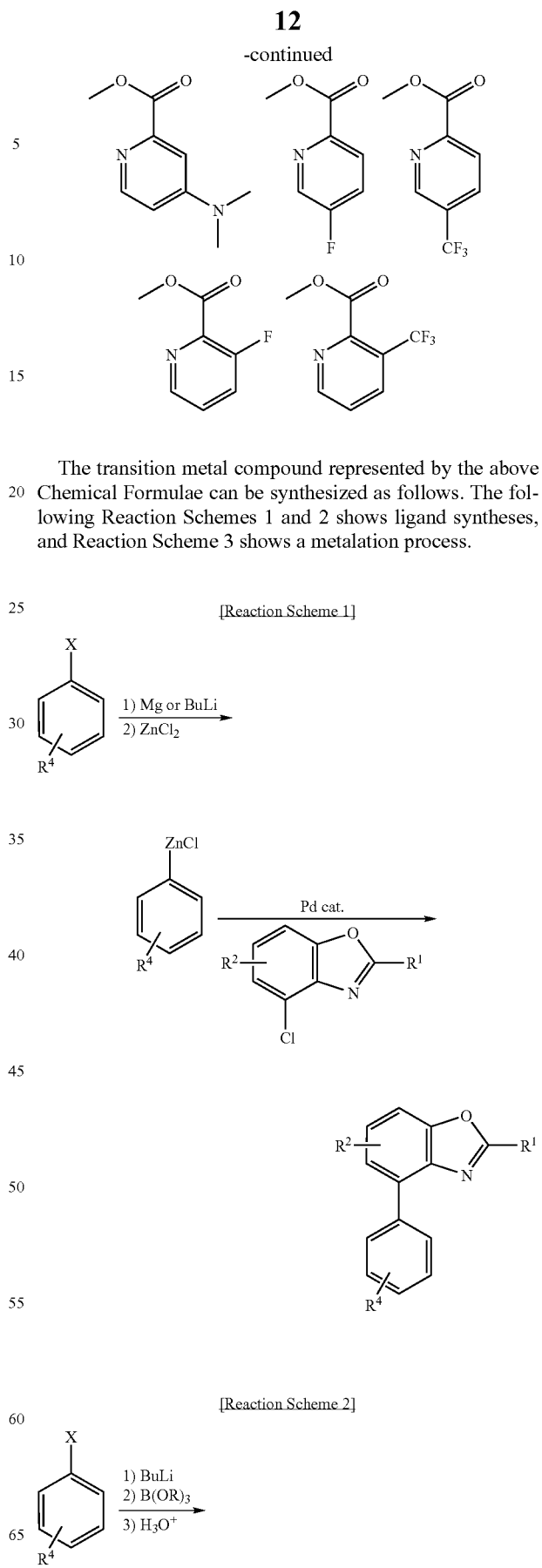
The transition metal compound represented by the above Chemical Formulae can be synthesized as follows. The following Reaction Schemes 1 and 2 shows ligand syntheses, and Reaction Scheme 3 shows a metalation process.
[Reaction Scheme 1]
[Reaction Scheme 2]

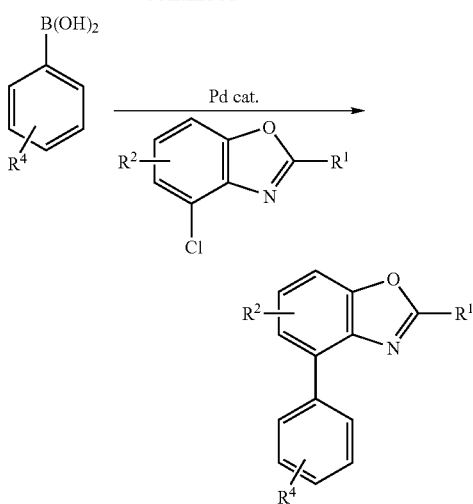

The Reaction Schemes 1 and 2 show similar yield and further the Reaction Scheme 2 is appropriate since in situ reaction can be performed.

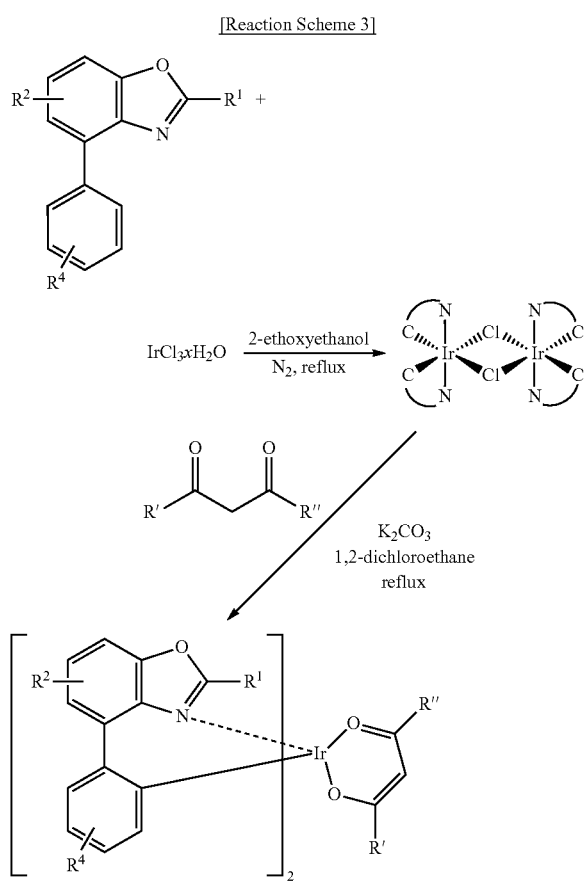

As shown in Reaction Scheme 3, the metalation process is as follows: a phenylene benzooxazole derivative and hydrated iridium trichloride are reacted under a nitrogen atmosphere to prepare a dimmer intermediate that includes two iridium metals sharing a Cl ligand, and then the intermediate is reacted with an auxiliary ligand in a solvent including a weak base to prepare the transition metal compound of Chemical Formula 2.

THE EFFECT OF THE INVENTION

The phosphor material is applied to an organic electroluminescence device to increase the lifespan of a light emitting material, to increase the luminous efficiency, and to reduce concentration quenching. It also applied to display devices, displays, backlights, electron photographs, illumination sources, light sources, signs, signboards, interiors, and so on. It can also be applied to display devices, displays, backlights, electron photographs, illumination sources, light sources, signs, signboards, interiors, and so on. Compared to a conventional fluorescent organic EL device having external quantum efficiency of less than 5%, power consumption can be significantly reduced. By introducing a substituent having steric hindrance, high efficiency can be maintained even at high doping concentration and thereby lifespan of a device increases. The compound of the present invention can be applied for medicals purposes, and to fluorescent brighteners, photographs, UV absorbents, laser dyes, dyes for a color filter, color conversion filters, and so on.

BEST MODE

The present invention can be specified by the following Examples. The Examples only illustrate the present invention and they do not limit the scope and range of the present invention, which is defined by the accompanying claims.

EXAMPLE 1

Compound 1: Synthesis of $(FMPBTZ)_2Ir(acac)$

Synthesis of 4-(4-(trifluoromethyl)phenyl)benzo[d]thiazole: a 500 mL 2-neck round-bottomed flask was equipped with a reflux condenser and replaced by nitrogen. 70 mL of THF that was dried with 0.11 mol of Mg metal was added to the above flask and then, 0.10 mol of 1-bromo-4-(trifluoromethyl)benzene was added in a dropwise fashion. The reaction was significantly exothermic and thus a cooling bath was equipped to reduce the temperature inside the reactor less than 50° C. It was agitated for 2 hours at room temperature, 0.11 mol of zinc chloride was added with 100 mL of THF, and further agitated for 2 hours to obtain a slurry-phase reaction mixture. Another flask was replaced by nitrogen and then 4-chlorobenzothiazole derivative (0.10 mol), Pd (0.10 mol), and $Pd(PPh_3)_4$ (3 mol %) were dissolved in 100 mL of THF. The prepared solution was added to the reaction mixture and then agitated at 60° C. for 24 hours. After the reaction is complete, the resulting product was placed on a silica gel column to remove an inorganic slurry, and then a THF solution was concentrated under vacuum to obtain 4-(4-(trifluoromethyl)phenyl)benzo[d]thiazole at a yield of 91% using column chromatography.

Synthesis of $(FMPBTZ)_2Ir(Cl)_2Ir(FMPBTZ)_2$: 5 mmol of FMPBTZ and 10 mmol of $IrCl_3xH_2O$ were dissolved in 100 mL of 2-ethoxyethanol and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(FMPBTZ)Ir(Cl)_2Ir(FMPBTZ)_2$ at a yield of 95%.

Synthesis of $(FMPBTZ)_2Ir(acac)$: 5 mmol of $(FMPBTZ)_2Ir(Cl)_2Ir(FMPBTZ)_2$ and 25 mmol of 2,4-pentadione, and 50 mmol of potassium carbonate were mixed in 10 mL of 1,2-dichloroethane and then refluxed under a nitrogen atmosphere for 24 hours. After the reaction was complete, the solution was cooled down into about 50° C. and filtrated. The filtrate solution was purified by using column chromatography to thereby produce (FMPBTZ)$_2$Ir(acac) at a yield of 88%.

EXAMPLE 2

Compound 2: Synthesis of (FMPBTZ)$_2$Ir(Facac)

5 mmol of (FMPBTZ)$_2$Ir(Cl)$_2$Ir(FMPBTZ)$_2$, 25 mmol of 1,1,1-trifluoropentane-2,4-dione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (FMPBTZ)$_2$Ir(Facac) at a yield of 91%.

EXAMPLE 3

Compound 3: Synthesis of (FMPBTZ)$_2$Ir(FacacF)

5 mmol of (FMPBTZ)$_2$Ir(Cl)$_2$Ir(FMPBTZ)$_2$, 25 mmol of 1,1,1,5,5,5-hexafluoropentane-2,4-dione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (FMPBTZ)$_2$Ir(FacacF) at a yield of 89%.

EXAMPLE 4

Compound 4: Synthesis of (FMPBTZ)$_2$Ir(Pic)

5 mmol of (FMPBTZ)$_2$Ir(Cl)$_2$Ir(FMPBTZ)$_2$, 25 mmol of picolinic acid, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (FMPBTZ)$_2$Ir(Pic) at a yield of 87%.

EXAMPLE 5

Compound 5: Synthesis of (FMPBTZ)$_2$Ir(NPic)

5 mmol of (FMPBTZ)$_2$Ir(Cl)$_2$Ir(FMPBTZ)$_2$, 25 mmol of 5-dimethylamino pyridine-2-carboxylic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (FMPBTZ)$_2$Ir(NPic) at a yield of 88%.

EXAMPLE 6

Compound 6: Synthesis of (TBTZ)$_2$Ir(acac)

Synthesis of 4-para-tolylbenzo[d]thiazole: a 500 mL 2-neck round-bottomed flask was equipped with a reflux condenser and replaced by nitrogen. 70 mL of THF that was dried with 0.11 mol of Mg metal was added to the above flask and then, 0.10 mol of 1-bromo-4-methylbenzene was added in a dropwise fashion. The reaction was significantly exothermic and thus a cooling bath was equipped to reduce the temperature inside the reactor less than 50° C. It was agitated for 2 hours at room temperature, 0.11 mol of zinc chloride was added with 100 mL of THF, and further agitated for 2 hours to obtain a slurry-phase reaction mixture. Another flask was replaced by nitrogen and then 0.10 mol of 4-chlorobenzothiazole derivative, 0.10 mol of Pd, and Pd(PPh$_3$)$_4$ (3 mol %) were dissolved in 100 mL of THF. The prepared solution was added to the reaction mixture and then agitated 60° C. for 24 hours. After the reaction is complete, the resulting product was placed on a silica gel column to remove an inorganic slurry, and then a THF solution was concentrated under vacuum to obtain 4-para-tolylbenzo[d]thiazole using column chromatography at a yield of 91%.

Synthesis of (TBTZ)$_2$Ir(Cl)$_2$Ir(TBTZ)$_2$: 5 mmol of TBTZ and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (TBTZ)Ir(Cl)$_2$Ir(TBTZ)$_2$ at a yield of 95%.

Synthesis of (TBTZ)$_2$Ir(acac): 5 mmol of (TBTZ)$_2$Ir(Cl)$_2$Ir(TTZ)$_2$, 25 mmol of 2,4-pentadione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (TBTZ)$_2$Ir(acac) at a yield of 90%.

EXAMPLE 7

Compound 7: Synthesis of Z(TBTZ)$_2$Ir(Facac)

5 mmol of (TBTZ)$_2$Ir(Cl)$_2$Ir(TBTZ)$_2$, 25 mmol of 1,1,1-trifluoropentane-2,4-dione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (TBTZ)$_2$Ir(Facac) at a yield of 92%.

EXAMPLE 8

Compound 8: Synthesis of (TBTZ)$_2$Ir(FacacF)

5 mmol of (TBTZ)$_2$Ir(Cl)$_2$Ir(TBTZ)$_2$, 25 mmol of 1,1,1,5,5,5-hexafluoropentane-2,4-dion, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (TBTZ)$_2$Ir(FacacF) at a yield of 88%.

EXAMPLE 9

Compound 9: Synthesis of (TBTZ)$_2$Ir(Pic)

5 mmol of (TBTZ)$_2$Ir(Cl)$_2$Ir(TBTZ)$_2$, 25 mmol of picolinic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (TBTZ)$_2$Ir(Pic) at a yield of 87%.

EXAMPLE 10

Compound 10: Synthesis of (TBTZ)$_2$Ir(NPic)

5 mmol of (TBTZ)$_2$Ir(Cl)$_2$Ir(TBTZ)$_2$, 25 mmol of 5-dimethylamino pyridine-2-carboxylic acid, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (TBTZ)$_2$Ir(NPic) at a yield of 89%.

EXAMPLE 11

Compound 11: Synthesis of (TBOZ)$_2$Ir(acac)

Synthesis of 4-para-tolylbenzo[d]oxazole: a 500 mL 2-neck round-bottomed flask was equipped with a reflux condenser and replaced by nitrogen. 70 mL of THF that was dried with 0.11 mol of Mg metal was added to the above flask and then, 0.10 mol of 1-bromo-4-methylbenzene was added in a dropwise fashion. The reaction was significantly exodermic and thus a cooling bath was equipped to reduce the temperature inside the reactor less than 50° C. It was agitated for 2 hours at room temperature, 0.11 mol of zinc chloride was added with 100 mL of THF, and further agitated for 2 hours to obtain a slurry-phase reaction mixture. Another flask was replaced by nitrogen and then 0.10 mol of 4-chlorobenzo[d]oxazole derivative, 0.10 mol of Pd, and 3 mol % of Pd(PPh$_3$)$_4$ were dissolved in 100 mL of THF. The prepared solution was added to the reaction mixture and then agitated 60° C. for 24 hours. After the reaction is complete, the resulting product was placed on a silica gel column to remove an inorganic slurry, and then a THF solution was concentrated under vacuum to obtain 4-para-tolylbenzo[d]oxazole using column chromatography at a yield of 91%.

Synthesis of (TBOZ)$_2$Ir(Cl)$_2$Ir(TBTZ)$_2$: 5 mmol of TBOZ and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (TBOZ)Ir(Cl)$_2$Ir(TBOZ)$_2$ at a yield of 95%.

Synthesis of (TBOZ)$_2$Ir(acac): 5 mmol of (TBOZ)$_2$Ir(Cl)$_2$Ir(TBOZ)$_2$, 25 mmol of 2,4-pentadione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (TBOZ)$_2$Ir(acac) at a yield of 90%.

EXAMPLE 12

Compound 12: Synthesis of (TBOZ)$_2$Ir(Facac)

5 mmol of (TBOZ)$_2$Ir(Cl)$_2$Ir(TBOZ)$_2$, 25 mmol of 1,1,1-trifluoropentane-2,4-dion, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (TBOZ)$_2$Ir(Facac) at a yield of 92%.

EXAMPLE 13

Compound 13: Synthesis of (TBOZ)$_2$Ir(FacacF)

5 mmol of (TBOZ)$_2$Ir(Cl)$_2$Ir(TBOZ)$_2$, 25 mmol of 1,1,1,5,5,5-hexafluoropentane-2,4-dion, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (TBOZ)$_2$Ir(FacacF) at a yield of 91%.

EXAMPLE 14

Compound 14: Synthesis of (TBOZ)$_2$Ir(Pic)

5 mmol of (TBOZ)$_2$Ir(Cl)$_2$Ir(TBOZ)$_2$, 25 mmol of picolinic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (TBOZ)$_2$Ir(Pic) at a yield of 91%.

EXAMPLE 15

Compound 15: Synthesis of (TBOZ)$_2$Ir(NPic)

5 mmol of (TBOZ)$_2$Ir(Cl)$_2$Ir(TBOZ)$_2$, 25 mmol of 5-dimethylamino pyridine-2-carboxylic acid, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (TBOZ)$_2$Ir(NPic) at a yield of 90%.

EXAMPLE 16

Compound 16: Synthesis of (FMPBOZ)$_2$Ir(acac)

Synthesis of 4-(4-(trifluoromethyl)phenyl)benzo[d]oxazole: a 500 mL 2-neck round-bottomed flask was equipped with a reflux condenser and replaced by nitrogen. 70 mL of THF that was dried with 0.11 mol of Mg metal was added to the above flask and then, 0.10 mol of 4-chlorobenzo[d]oxazole was added in a dropwise fashion. The reaction was significantly exodermic and thus a cooling bath was equipped to reduce the temperature inside the reactor less than 50° C. It was agitated for 2 hours at room temperature, 0.11 mol of zinc chloride was added with 100 mL of THF, and further agitated for 2 hours to obtain a slurry-phase reaction mixture. Another flask was replaced by nitrogen and then 0.10 mol of 4-chlorobenzo[d]oxazole derivative, 0.10 mol of Pd, and 3 mol % of Pd(PPh$_3$)$_4$ were dissolved in 100 mL of THF. The prepared solution was added to the reaction mixture and then agitated 60° C. for 24 hours. After the reaction is complete, the resulting product was placed on a silica gel column to remove an inorganic slurry, and then a THF solution was concentrated under vacuum to obtain 4-(4-(trifluoromethyl)phenyl)benzo[d]oxazole using column chromatography at a yield of 91%.

Synthesis of (FMPBOZ)$_2$Ir(Cl)$_2$Ir(FMPBOZ)$_2$: 5 mmol of FMPBOZ and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (FMPBTZ)Ir(Cl)$_2$Ir(FMPBOZ)$_2$ at a yield of 95%.

Synthesis of (FMPBOZ)$_2$Ir(acac): 5 mmol of (FMPBOZ)$_2$Ir(Cl)$_2$Ir(FMPBOZ)$_2$, 25 mmol of 2,4-pentadione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (FMPBOZ)$_2$Ir(acac) at a yield of 88%.

EXAMPLE 17

Compound 17: Synthesis of (FMPBOZ)$_2$Ir(Facac)

5 mmol of (FMPBOZ)$_2$Ir(Cl)$_2$Ir(FMPBOZ)$_2$, 25 mmol of 1,1,1-trifluoropentane-2,4-dione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (FMPBOZ)$_2$Ir(Facac) at a yield of 84%.

EXAMPLE 18

Compound 18: Synthesis of (FMPBOZ)$_2$Ir(FacacF)

5 mmol of (FMPBOZ)$_2$Ir(Cl)$_2$Ir(FMPBOZ)$_2$, 25 mmol of 1,1,1,5,5,5-hexafluoropentane-2,4-dione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (FMPBOZ)$_2$Ir(FacacF) at a yield of 83%.

EXAMPLE 19

Compound 19: Synthesis of (FMPBOZ)$_2$Ir(Pic)

5 mmol of (FMPBOZ)$_2$Ir(Cl)$_2$Ir(FMPBOZ)$_2$, 25 mmol of picolinic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (FMPBOZ)$_2$Ir(Pic) at a yield of 85%.

EXAMPLE 20

Compound 20: Synthesis of (FMPBOZ)$_2$Ir(NPic)

5 mmol of (FMPBOZ)$_2$Ir(Cl)$_2$Ir(FMPBOZ)$_2$, 25 mmol of 5-dimethylamino pyridine-2-carboxylic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (FMPBOZ)$_2$Ir(NPic) at a yield of 87%.

EXAMPLE 21

Compound 21: Synthesis of (HFPBTZ)$_2$Ir(acac)

Synthesis of 4-(4-(1,1,1,3,3,3-hexafluoropropane-2-yl)phenyl)benzo[d]thiazole: a 500 mL 2-neck round-bottomed flask was equipped with a reflux condenser and replaced by nitrogen. 70 mL of THF that was dried with 0.11 mol of Mg metal was added to the above flask and then, 0.10 mol of 1-bromo-4-(1,1,1,3,3,3-hexafluoropropane-2-yl)benzene was added in a dropwise fashion. The reaction was significantly exodermic and thus a cooling bath was equipped to reduce the temperature inside the reactor less than 50° C. It was agitated for 2 hours at room temperature, 0.11 mol of zinc chloride was added with 100 mL of THF, and further agitated for 2 hours to obtain a slurry-phase reaction mixture. Another flask was replaced by nitrogen and then 0.10 mol of 4-chlorobenzothiazole derivative, 0.10 mol of Pd, and 3 mol % of Pd(PPh$_3$)$_4$ were dissolved in 100 mL of THF. The prepared solution was added to the reaction mixture and then agitated 60° C. for 24 hours. After the reaction is complete, the resulting product was placed on a silica gel column to remove an inorganic slurry, and then a THF solution was concentrated under vacuum to obtain 4-(4-(1,1,1,3,3,3-hexafluoropropane-2-yl)phenyl)benzo[d]thiazole using column chromatography at a yield of 91%.

Synthesis of (HFPBTZ)$_2$Ir(Cl)$_2$Ir(HFPBTZ)$_2$: 5 mmol of HFPBTZ and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (HFPBTZ)Ir(Cl)$_2$Ir(HFPBTZ)$_2$ at a yield of 95%.

Synthesis of (HFPBTZ)$_2$Ir(acac): 5 mmol of (HFPBTZ)$_2$Ir(Cl)$_2$Ir(HFPBTZ)$_2$, 25 mmol of 2,4-pentadione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (HFPBTZ)$_2$Ir(acac) at a yield of 90%.

EXAMPLE 22

Compound 22: Synthesis of (HFPBTZ)$_2$Ir(Facac)

5 mmol of (HFPBTZ)$_2$Ir(Cl)$_2$Ir(HFPBTZ)$_2$, 25 mmol of 1,1,1-trifluoropentane-2,4-dione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (HFPBTZ)$_2$Ir(Facac) at a yield of 89%.

EXAMPLE 23

Compound 23: Synthesis of (HFPBTZ)$_2$Ir(FacacF)

5 mmol of (HFPBTZ)$_2$Ir(Cl)$_2$Ir(HFPBTZ)$_2$, 25 mmol of 1,1,1,5,5,5-hexafluoropentane-2,4-dione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (HFPBTZ)$_2$Ir(FacacF) at a yield of 90%.

EXAMPLE 24

Compound 24: Synthesis of (HFPBTZ)$_2$Ir(Pic)

5 mmol of (HFPBTZ)$_2$Ir(Cl)$_2$Ir(HFPBTZ)$_2$, 25 mmol of picolinic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (HFPBTZ)$_2$Ir(Pic) at a yield of 91%.

EXAMPLE 25

Compound 25: Synthesis of (HFPBTZ)$_2$Ir(NPic)

5 mmol of (HFPBTZ)$_2$Ir(Cl)$_2$Ir(HFPBTZ)$_2$, 25 mmol of 5-dimethylamino pyridine-2-carboxylic acid, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (HFPBTZ)$_2$Ir(NPic) at a yield of 93%.

EXAMPLE 26

Compound 26: Synthesis of (HFPBOZ)$_2$Ir(acac)

Synthesis of 4-(4-(1,1,1,3,3,3-hexafluoropropane-2-yl)phenyl)benzo[d]oxazole: a 500 mL 2-neck round-bottomed flask was equipped with a reflux condenser and replaced by nitrogen. 70 mL of THF that was dried with 0.11 mol of Mg metal was added to the above flask and then, 1-bromo-4-0.10 mol of (1,1,1,3,3,3-hexafluoropropham-2-yl)benzene was added in a dropwise fashion. The reaction was significantly exodermic and thus a cooling bath was equipped to reduce the temperature inside the reactor less than 50° C. It was agitated for 2 hours at room temperature, 0.11 mol of zinc chloride was added with 100 mL of THF, and further agitated for 2 hours to obtain a slurry-phase reaction mixture. Another flask was replaced by nitrogen and then 0.10 mol of 4-chlorobenzo[d]oxazole derivative, 0.10 mol of Pd, and 3 mol % of Pd(PPh$_3$)$_4$ were dissolved in 100 mL of THF. The prepared solution was added to the reaction mixture and then agitated 60° C. for 24 hours. After the reaction is complete, the resulting product was placed on a silica gel column to remove an inorganic slurry, and then a THF solution was concentrated under vacuum to obtain 4-(4-(1,1,1,3,3,3-hexafluoropropane-2-yl)phenyl)benzo[d]oxazole at a yield of 91% using column chromatography.

Synthesis of (HFPBOZ)$_2$Ir(Cl)$_2$Ir(HFPBOZ)$_2$: 5 mmol of HFPBOZ and 10 mmol of IrCl$_3$xH$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce (HFPBOZ)Ir(Cl)$_2$Ir(HFPBOZ)$_2$ at a yield of 95%.

Synthesis of (HFPBOZ)$_2$Ir(acac): 5 mmol of (HFPBOZ)$_2$Ir(Cl)$_2$Ir(BFPBOZ)$_2$, 25 mmol of 2,4-pentadione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (HFPBOZ)$_2$Ir(acac) at a yield of 92%.

EXAMPLE 27

Compound 27: Synthesis of (HFPBOZ)$_2$Ir(Facac)

5 mmol of (HFPBOZ)$_2$Ir(Cl)$_2$Ir(HFPBOZ)$_2$, 25 mmol of 1,1,1-trifluoropentane-2,4-dione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (HFPBOZ)$_2$Ir(Facac) at a yield of 85%.

EXAMPLE 28

Compound 28: Synthesis of (HFPBOZ)$_2$Ir(FacacF)

5 mmol of (HFPBOZ)$_2$Ir(Cl)$_2$Ir(HFPBOZ)$_2$, 25 mmol of 1,1,1,5,5,5-hexafluoropentane-2,4-dione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (HFPBOZ)$_2$Ir(FacacF) at a yield of 87%.

EXAMPLE 29

Compound 29: Synthesis of (HFPBOZ)$_2$Ir(Pic)

5 mmol of (HFPBOZ)$_2$Ir(Cl)$_2$Ir(HFPBOZ)$_2$, 25 mmol of picolinic acid, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (HFPBOZ)$_2$Ir(Pic) at a yield of 90%.

EXAMPLE 30

Compound 30: Synthesis of (HFPBOZ)$_2$Ir(NPic)

5 mmol of (HFPBOZ)$_2$Ir(Cl)$_2$Ir(HFPBOZ)$_2$, 25 mmol of 5-dimethylamino pyridine-2-carboxylic acid, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (HFPBOZ)$_2$Ir(NPic) at a yield of 92%.

EXAMPLE 31

Compound 31: Synthesis of (PBTZ)$_2$Ir(acac)

Synthesis of 4-phenylbenzo[d]thiazole: a 500 mL 2-neck round-bottomed flask was equipped with a reflux condenser and replaced by nitrogen. 70 mL of THF that was dried with Mg metal (0.11 mol) was added to the above flask and then, 1-bromobenzene (0.10 mol) was added in a dropwise fashion. The reaction was significantly exodermic and thus a cooling bath was equipped to reduce the temperature inside the reactor less than 50° C. It was agitated for 2 hours at room temperature, zinc chloride (0.1 μmol) was added with 100 mL of THF, and further agitated for 2 hours to obtain a slurry-phase reaction mixture. Another flask was replaced by nitrogen and then 0.10 mol of 4-chlorobenzothiazole derivative, 0.10 mol of Pd, and 3 mol % of $Pd(PPh_3)_4$ were dissolved in 100 mL of THF. The prepared solution was added to the reaction mixture and then agitated 60° C. for 24 hours. After the reaction is complete, the resulting product was placed on a silica gel column to remove an inorganic slurry, and then a THF solution was concentrated under vacuum to obtain 4-phenylbenzo[d]thiazole using column chromatography at a yield of 91%.

Synthesis of $(PBTZ)_2Ir(Cl)_2Ir(PBTZ)_2$: 5 mmol of PBTZ and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBTZ)Ir(Cl)_2Ir(PBTZ)_2$ at a yield of 94%.

Synthesis of $(PBTZ)_2Ir(acac)$: 5 mmol of $(PBTZ)_2Ir(Cl)_2Ir(PBTZ)_2$, 25 mmol of 2,4-pentadione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce $(PBTZ)_2Ir(acac)$ at a yield of 85%.

EXAMPLE 32

Compound 32: Synthesis of $(PBTZ)_2Ir(Facac)$ 5 mmol of $(PBTZ)_2Ir(Cl)_2Ir(PBTZ)_2$, 25 mmol of 1,1,1-trifluoropentane-2,4-dione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce $(PBTZ)_2Ir(Facac)$ at a yield of 89%.

EXAMPLE 33

Compound 33: Synthesis of $(PBTZ)_2Ir(FacacF)$ 5 mmol of $(PBTZ)_2Ir(Cl)_2Ir(PBTZ)_2$, 25 mmol of 1,1,1,5,5,5-hexafluoropentane-2,4-dione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce $(PBTZ)_2Ir(FacacF)$ at a yield of 87%.

EXAMPLE 34

Compound 34: Synthesis of $(PBTZ)_2Ir(Pic)$ 5 mmol of $(PBTZ)_2Ir(Cl)_2Ir(PBTZ)_2$, 25 mmol of picolinic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce $(PBTZ)_2Ir(Pic)$ at a yield of 92%.

EXAMPLE 35

Compound 35: Synthesis of $(PBTZ)_2Ir(NPic)$ 5 mmol of $(PBTZ)_2Ir(Cl)_2Ir(PBTZ)_2$, 25 mmol of 5-dimethylamino pyridine-2-carboxylic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce $(PBTZ)_2Ir(NPic)$ at a yield of 91%.

EXAMPLE 36

Compound 36: Synthesis of $(PBOZ)_2Ir(acac)$

Synthesis of 4-phenylbenzo[d]oxazole: a 500 mL 2-neck round-bottomed flask was equipped with a reflux condenser and replaced by nitrogen. 70 mL of THF that was dried with 0.11 mol of Mg metal was added to the above flask and then, 0.10 mol of 1-bromobenzene was added in a dropwise fashion. The reaction was significantly exodermic and thus a cooling bath was equipped to reduce the temperature inside the reactor less than 50° C. It was agitated for 2 hours at room temperature, 0.11 mol of zinc chloride was added with 100 mL of THF, and further agitated for 2 hours to obtain a slurry-phase reaction mixture. Another flask was replaced by nitrogen and then 0.10 mol of 4-chlorobenzo[d]oxazole derivative, 0.10 mol of Pd, and 3 mol % of $Pd(PPh_3)_4$ were dissolved in 100 mL of THF. The prepared solution was added to the reaction mixture and then agitated 60° C. for 24 hours. After the reaction is complete, the resulting product was placed on a silica gel column to remove an inorganic slurry, and then a THF solution was concentrated under vacuum to obtain 4-phenylbenzo[d]oxazole using column chromatography at a yield of 89%.

Synthesis of $(PBOZ)_2Ir(Cl)_2Ir(PBOZ)_2$: 5 mmol of PBOZ and 10 mmol of $IrCl_3xH_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtrated, rinsed with water and an ether solvent, and dried to thereby produce $(PBOZ)Ir(Cl)_2Ir(PBOZ)_2$ at a yield of 93%.

Synthesis of $(PBOZ)_2Ir(acac)$: 5 mmol of $(PBOZ)_2Ir(Cl)_2Ir(PBOZ)_2$, 25 mmol of 2,4-pentadione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce $(PBOZ)_2Ir(acac)$ at a yield of 84%.

EXAMPLE 37

Compound 37: Synthesis of $(PBOZ)_2Ir(Facac)$ 5 mmol of $(PBOZ)_2Ir(Cl)_2Ir(PBOZ)_2$, 25 mmol of 1,1,1-trifluoropentane-2,4-dione, and 50 mmol of potassium carbonate were mixed in 100 mL of 1,2-dichloroethane and refluxed for 24 hours under a nitrogen atmosphere. After the reaction was complete, the solution was cooled down into about 50° C. and filtrated. The filtrate solution was purified by using column chromatography to thereby produce (PBOZ)$_2$Ir (Facac) at a yield of 81%.

EXAMPLE 38

Compound 38: Synthesis of (PBOZ)$_2$Ir(FacacF)

5 mmol of (PBOZ)$_2$Ir(Cl)$_2$Ir(PBOZ)$_2$, 25 mmol of 1,1,1, 5,5,5-hexafluoropentane-2,4-dione, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (PBOZ)$_2$Ir (FacacF) at a yield of 82%.

EXAMPLE 39

Compound 39: Synthesis of (PBOZ)$_2$Ir(Pic)

5 mmol of (PBOZ)$_2$Ir(Cl)$_2$Ir(PBOZ)$_2$, 25 mmol of picolinic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (PBOZ)$_2$Ir(Pic) at a yield of 92%.

EXAMPLE 40

Compound 40: Synthesis of (PBOZ)$_2$Ir(NPic)

5 mmol of (PBOZ)$_2$Ir(Cl)$_2$Ir(PBOZ)$_2$, 25 mmol of 5-dimethylamino pyridine-2-carboxylic acid, and 50 mmol of potassium carbonate were mixed in 100 mL of 1,2-dichloroethane, and refluxed for 24 hours under a nitrogen atmosphere. After the reaction was complete, the solution was cooled down into about 50° C. and filtrated. The filtrate solution was purified by using column chromatography to thereby produce (PBOZ)$_2$Ir(NPic) at a yield of 88%.

PL spectra of the above chemical compounds were acquired and the results were presented in the following Table 1.

TABLE 1

| Compound | Yield (%) | PL (nm) |
|---|---|---|
| Compound 1 | 88 | 579 |
| Compound 2 | 91 | 573 |
| Compound 3 | 89 | 570 |
| Compound 4 | 87 | 576 |
| Compound 5 | 88 | 572 |
| Compound 6 | 90 | 602 |
| Compound 7 | 92 | 595 |
| Compound 8 | 88 | 593 |
| Compound 9 | 87 | 596 |
| Compound 10 | 89 | 594 |
| Compound 11 | 90 | 582 |
| Compound 12 | 92 | 579 |
| Compound 13 | 91 | 577 |
| Compound 14 | 91 | 579 |
| Compound 15 | 90 | 575 |
| Compound 16 | 88 | 569 |
| Compound 17 | 84 | 562 |
| Compound 18 | 83 | 561 |
| Compound 19 | 85 | 564 |
| Compound 20 | 89 | 561 |
| Compound 21 | 90 | 558 |
| Compound 22 | 89 | 552 |
| Compound 23 | 90 | 551 |
| Compound 24 | 91 | 554 |
| Compound 25 | 93 | 551 |
| Compound 26 | 92 | 547 |
| Compound 27 | 85 | 544 |
| Compound 28 | 87 | 541 |
| Compound 29 | 90 | 545 |
| Compound 30 | 92 | 540 |
| Compound 31 | 85 | 604 |
| Compound 32 | 89 | 595 |
| Compound 33 | 87 | 594 |
| Compound 34 | 92 | 597 |
| Compound 35 | 91 | 594 |
| Compound 36 | 84 | 579 |
| Compound 37 | 81 | 574 |
| Compound 38 | 82 | 571 |
| Compound 39 | 92 | 577 |
| Compound 40 | 88 | 572 |

EXAMPLE 41

As for an anode, a 10 Ω/cm$^2$ ITO substrate produced by the Corning Company was used. A hole injection layer was formed in a thickness of 60 nm by depositing IDE406 on top of the substrate in a vacuum condition. Subsequently, a hole transport layer was formed by depositing TPD chemical compound on top of the hole injection layer in a thickness of 30 nm in a vacuum condition. A light emitting layer was formed in a thickness of 20 nm by depositing a transition metal compound on top of the hole transport layer in a vacuum condition.

Subsequently, an HBL layer was formed in a thickness of 5 nm by depositing BCP on top of the light emitting layer in a vacuum condition. An electron transport layer (ETL) was formed in a thickness of 20 nm by depositing Alq3 on top of the light emitting layer in a vacuum condition. An organic electroluminescence device was completed by sequentially depositing LiF 1 nm and Al 300 nm on top of the electron transport layer in a vacuum condition to thereby form a LiF/Al electrode.

The luminance, color coordinates and efficiency of the organic electroluminescence device prepared according to Example 41 were measured.

As a result of the measurement, it can be confirmed that the organic electroluminescence device can be operated at a low voltage and implements high efficiency indicating that the metallic compound as an organic electro-luminescence material has excellent characteristics.

Simple modifications and alternations of the present invention can be easily made by the ordinary skilled person in the art within the spirit and scope of the appended claims.

The invention claimed is:

1. A metallic compound represented by the following Chemical Formula 1:

[Chemical Formula 1]

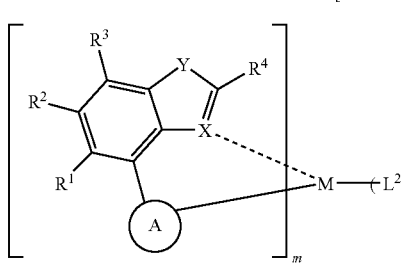

Wherein, M is a transition metal selected from Ir, Pt, Rh, Re, and Os, m is 2 or 3, n is 0 or 1, the sum of m and n is 3, provided that the sum of m and n is 2 when M is Pt,
X is N or P,
Y is S, O, or Se,

of the Chemical Formula 1 is represented by the following Chemical Formula 2:

[Chemical Formula 2]

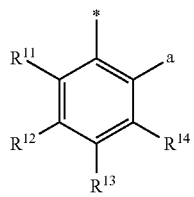

wherein, in the above Chemical Formulae 2, * denotes a portion that is covalently bound with adjacent aromatic portion, the transition metal M forms a complex while bound with a portion denoted as "a" in the above Chemical Formulae 2 by a covalent bond and bound with X of the Chemical Formula 1 by a coordination bond, $R^1$-$R^3$, and $R^5$-$R^{14}$ are hydrogen, a C1 to C20 alkyl, an aryl, a cycloalkyl, a halogen, a linear or branched substituent including at least one halogen, a linear or branched substituent including at least one heteroatom, carbonyl, vinyl, or acetylenyl, or form a cycle, and are the same or different, $R^4$ is hydrogen, a C1 to C20 alkyl excluding an aromatic cyclic substituent, a cycloalkyl, a halogen, a linear or branched substituent including at least one halogen, or a linear or branched substituent including at least one heteroatom, and $L^2$ of the Chemical Formula 1 is represented by the following Chemical Formula 4:

[Chemical Formula 4]

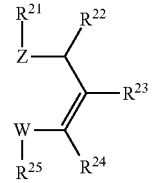

wherein
Z and W in the above Chemical Formula 4 are the same or different and a heteroatom of O, N, S, or P, and
$R^{21}$-$R^{25}$ in the Chemical Formula 4 are the same or different, and are selected from hydrogen, a C1 to C20 alkyl, an aryl, a cycloalkyl, a halogen, a linear or branched substituent including at least one halogen, a linear or branched substituent including at least one heteroatom, carbonyl, vinyl, or acetylenyl, or form a cycle.

* * * * *